(12) United States Patent
Parthasaradhi Reddy et al.

(10) Patent No.: US 10,815,204 B2
(45) Date of Patent: Oct. 27, 2020

(54) PROCESS FOR THE PREPARATION OF DIPHENYLPYRAZINE DERIVATIVES

(71) Applicant: HONOUR (R&D), Hyderabad (IN)

(72) Inventors: Bandi Parthasaradhi Reddy, Hyderabad (IN); Kura Rathnakar Reddy, Hyderabad (IN); Bandi Vamsi Krishna, Hyderabad (IN); Kesireddy Subhash Chander Reddy, Hyderabad (IN); Kancharla Rajendar Reddy, Hyderabad (IN)

(73) Assignee: Honour (R&D) (IN)

(*) Notice: Subject to any disclaimer, the term of this patent is extended or adjusted under 35 U.S.C. 154(b) by 0 days.

(21) Appl. No.: 16/088,965

(22) PCT Filed: Apr. 1, 2017

(86) PCT No.: PCT/IB2017/051881
§ 371 (c)(1),
(2) Date: Sep. 27, 2018

(87) PCT Pub. No.: WO2017/168401
PCT Pub. Date: Oct. 5, 2017

(65) Prior Publication Data
US 2019/0112277 A1    Apr. 18, 2019

(30) Foreign Application Priority Data

Apr. 1, 2016 (IN) .............. 201641011626

(51) Int. Cl.
| | |
|---|---|
| *C07D 241/20* | (2006.01) |
| *C07C 211/06* | (2006.01) |
| *A61K 31/495* | (2006.01) |
| *C07C 211/05* | (2006.01) |
| *C07C 211/07* | (2006.01) |
| *C07C 211/08* | (2006.01) |
| *A61K 31/4965* | (2006.01) |
| *C07D 295/03* | (2006.01) |

(52) U.S. Cl.
CPC .......... *C07D 241/20* (2013.01); *A61K 31/495* (2013.01); *A61K 31/4965* (2013.01); *C07C 211/05* (2013.01); *C07C 211/06* (2013.01); *C07C 211/07* (2013.01); *C07C 211/08* (2013.01); *C07D 295/03* (2013.01); *C07B 2200/13* (2013.01)

(58) Field of Classification Search
CPC .................................................... C07D 241/20
See application file for complete search history.

(56) References Cited

U.S. PATENT DOCUMENTS

| | | |
|---|---|---|
| 2013/0005742 A1 | 1/2013 | Harbeson et al. |
| 2014/0155414 A1 | 6/2014 | Itou et al. |

FOREIGN PATENT DOCUMENTS

| | | | |
|---|---|---|---|
| WO | 2017029594 A1 | | 2/2017 |
| WO | WO 2017/042828 | * | 3/2017 |

OTHER PUBLICATIONS

International Search Report for PCT/IB2017/051881 dated Jul. 7, 2017.
Asaki et al. Selexipag: An Oral and Selective IP Prostacyclin Receptor Agonist for the Treatment of Pulmonary Arterial Hypertension. J. Med. Chem., 58 (18) 7128-7137, 2015.

* cited by examiner

*Primary Examiner* — Brian E McDowell
(74) *Attorney, Agent, or Firm* — Caesar Rivise, PC

(57) ABSTRACT

The present invention relates to a process for the preparation of amorphous Selexipag from Selexipag crystalline salts using a solvent.

4 Claims, 5 Drawing Sheets

PROCESS FOR THE PREPARATION OF DIPHENYLPYRAZINE DERIVATIVES

CROSS REFERENCE TO RELATED APPLICATIONS

This United States national phase application claims the benefit under 35 U.S.C. § 371 of PCT Application No. PCT/IB2017/051881 filed on Apr. 1, 2017, which in turn claims priority to Indian Application Serial No. IN201641011626 filed on Apr. 1, 2016 and all of whose entire disclosures are incorporated by reference herein.

FIELD OF THE INVENTION

The present invention relates to a process for the preparation of diphenylpyrazine derivatives.

BACKGROUND OF THE INVENTION

Selexipag (Uptravi®), chemically known as 2-{4-[(5,6-diphenylpyrazin-2-yl)(isopropyl)amino]butoxy}-N-(methylsulfonyl)acetamide a compound of formula I is indicated for the treatment of pulmonary arterial hypertension (PAH). The compound of formula I has an excellent PGI2 receptor agonistic activity, platelet aggregation inhibitory action, vasodilating action, bronchial muscle dilating action, lipid deposition inhibitory effect, leukocyte activation inhibitory action and the like

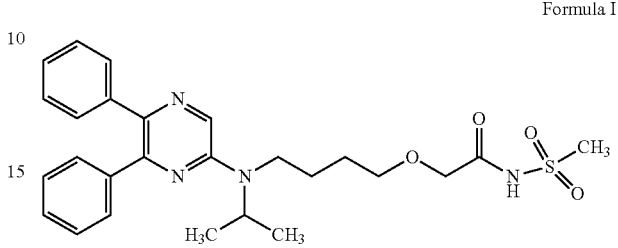

Formula I

U.S. Pat. No. 7,205,302 B2 (US'302) discloses Selexipag and its pharmaceutically acceptable salts thereof. US '302 discloses the following scheme for the preparation of Selexipag.

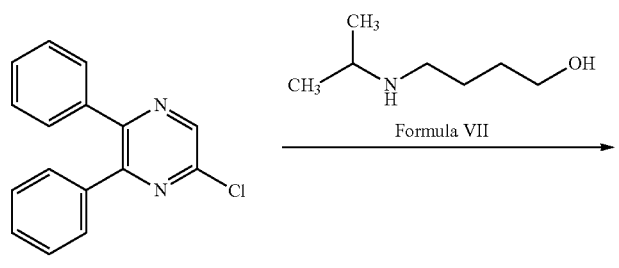

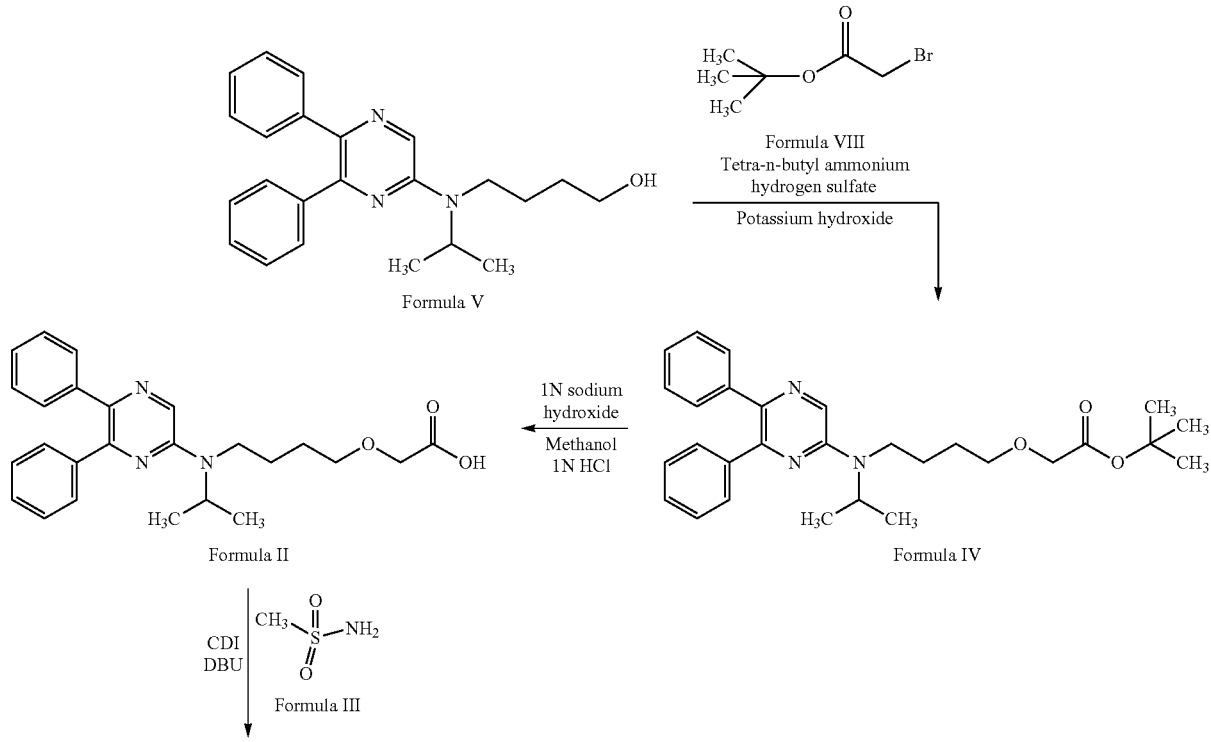

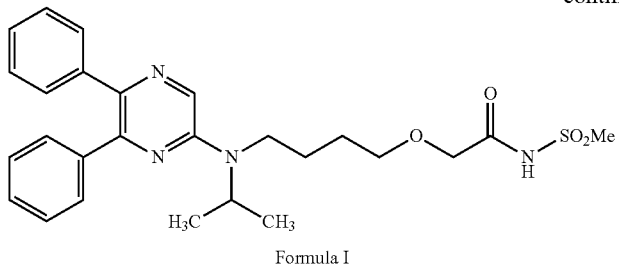

Formula I

WO 2011024874 A1 discloses the base addition salts of compound of formula I wherein the base is selected from t-butylamine, potassium, sodium and dimethylaminoethanol. Further this patent application discloses the Type I crystal of the t-butylamine salt, Form I crystal of the potassium salt, crystalline Form II of the potassium salt, Type III crystal of the potassium salt, Type VI crystal of the potassium salt, Form I crystals of sodium salt, Form II crystals of sodium salt, type III crystal of the sodium salt, Type IV crystal of the sodium salt, V-form crystals of the sodium salt, dimethylamino ethanolate Type I crystals of salt, dimethylamino ethanolate II-form crystals of salt. Moreover this application state that by considering the availability of pKa and the Selexipag, 5 species of the acid (hydrogen chloride, sulfuric acid, p-toluenesulfonic acid, methanesulfonic acid, benzenesulfonic acid) and 14 species of base (potassium hydroxide, sodium hydroxide, L-arginine, calcium hydroxide, magnesium hydroxide, choline, L-lysine, t-butylamine, ethylenediamine, ammonia, dimethylaminoethanol, N-methylglucamine, tromethamine, hydroxyethyl morpholine) were selected, results of Compound of formula I and their acid or base were investigated intensively or a salt formation, Compound I is found to form a limited salts with bases.

As per the present inventors, the prior art process found to be cumbersome industrially not applicable in view of use of multiple solvents for single step preparation i.e., for condensation tetrahydrofuran solvent thereafter work-up and isolation using diethylether. Further it has been observed that for the reaction using the mentioned solvents leads to completion of the reaction minimum 32 hours, which is time consuming and not acceptable industrially/commercially.

Further the prior art process involves the removal of 1,1'-Carbonyldiimidazole by column purification which is tedious and hence not suitable in commercial scale.

The present inventors have found that in addition to the base addition salts disclosed there are other salts which are more easily isolated as crystalline forms and which enhances the purity of final active pharmaceutical ingredient.

In view of the above, the present inventors have found a process for the preparation of Selexipag, which is suitable industrially, commercially and having high yields with acceptable purities.

OBJECTIVES OF THE INVENTION

The objective of the present invention is to provide a process for the preparation of Selexipag, which is commercially and industrially feasible.

Another objective of the present invention is to provide a process for the preparation of Selexipag, which results in high yield and high purity.

Another objective of the present invention is to provide Selexipag crystalline salts and their process.

Another objective of the present invention is to provide process for the preparation of amorphous form of Selexipag.

SUMMARY OF THE INVENTION

The present invention relates to a process for the preparation of Selexipag compound of Formula I, which comprises:

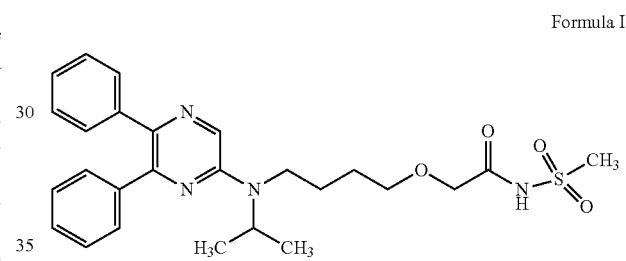

Formula I a. reacting the compound of formula II

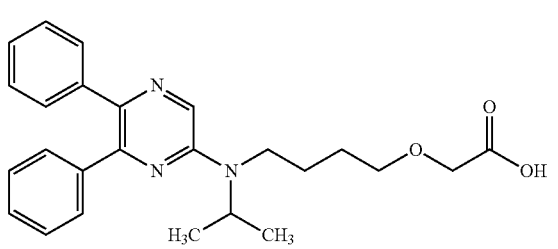

Formula II with a compound of formula III

Formula III in the presence of a condensing agent and a solvent;
b. adjusting the pH of the reaction mass by using a buffer, acetic acid;
c. optionally separating the layers and removing the solvent; and
d. isolating the Selexipag of formula I.

In another aspect the present invention relates to Selexipag crystalline salts, wherein the salt is selected from the group consisting of triethylamine, isopropylamine, tri n-butylamine, N-methylmorpholine, diisopropylethylamine.

In another embodiment of the present invention relates to a process for the preparation of Selexipag crystalline salts, which comprises:
a. treating Selexipag with base in a solvent; and
b. isolating the Selexipag crystalline salt;
wherein the base is selected from the group consisting of triethylamine, isopropylamine, tri n-butylamine, N-Methylmorpholine, diisopropylethylamine.

In another embodiment of the present invention relates to a process for the preparation of Selexipag in amorphous form, which comprises:
a. dissolving Selexipag crystalline salt in a low boiling solvent;
b. optionally treating with a buffer, acetic acid; and
c. removing the solvent to obtain Selexipag in amorphous form.

Figure 1:
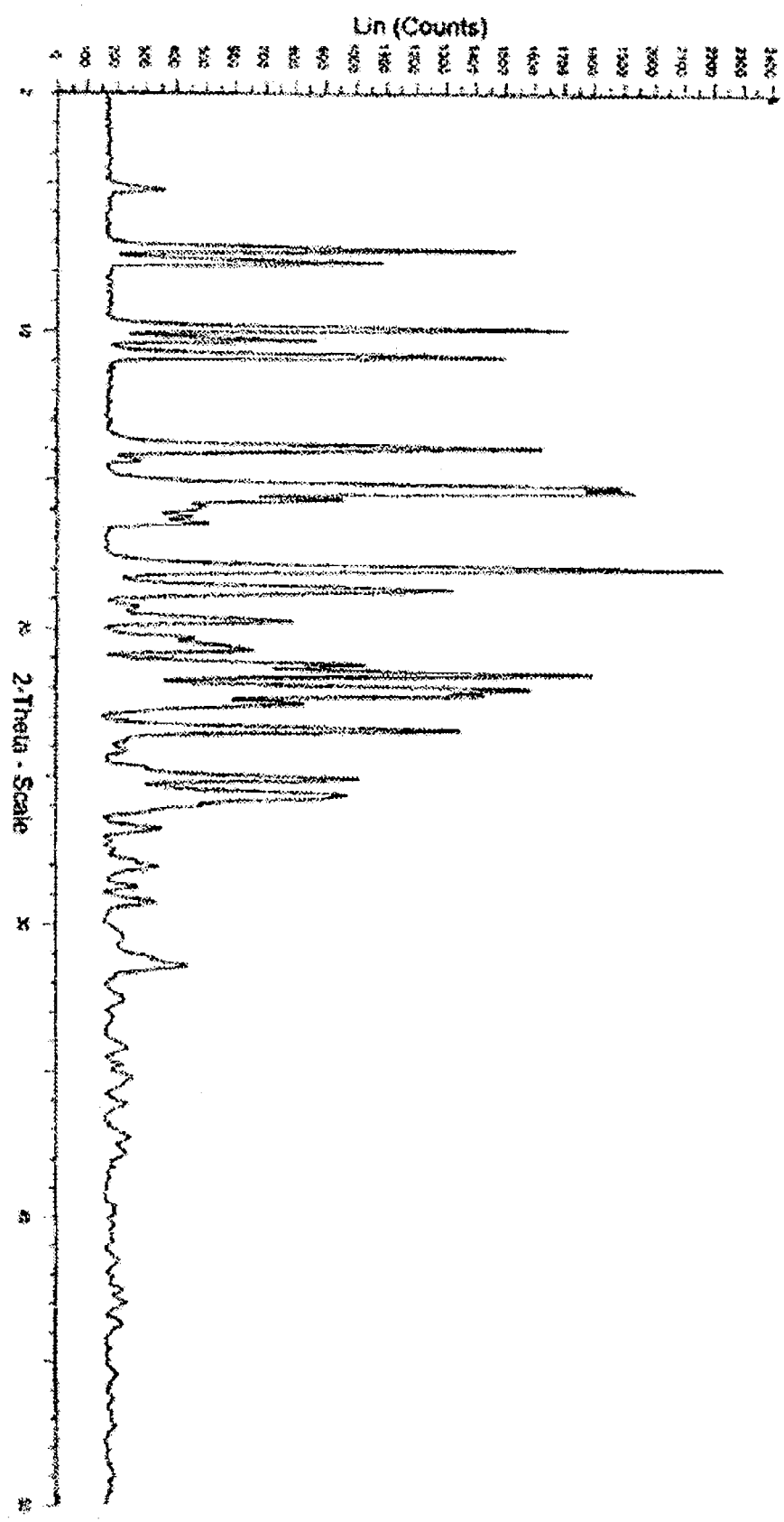
FIG. 1 shows powder X-ray diffractogram pattern of Selexipag triethylamine crystalline salt.
Figure 2:
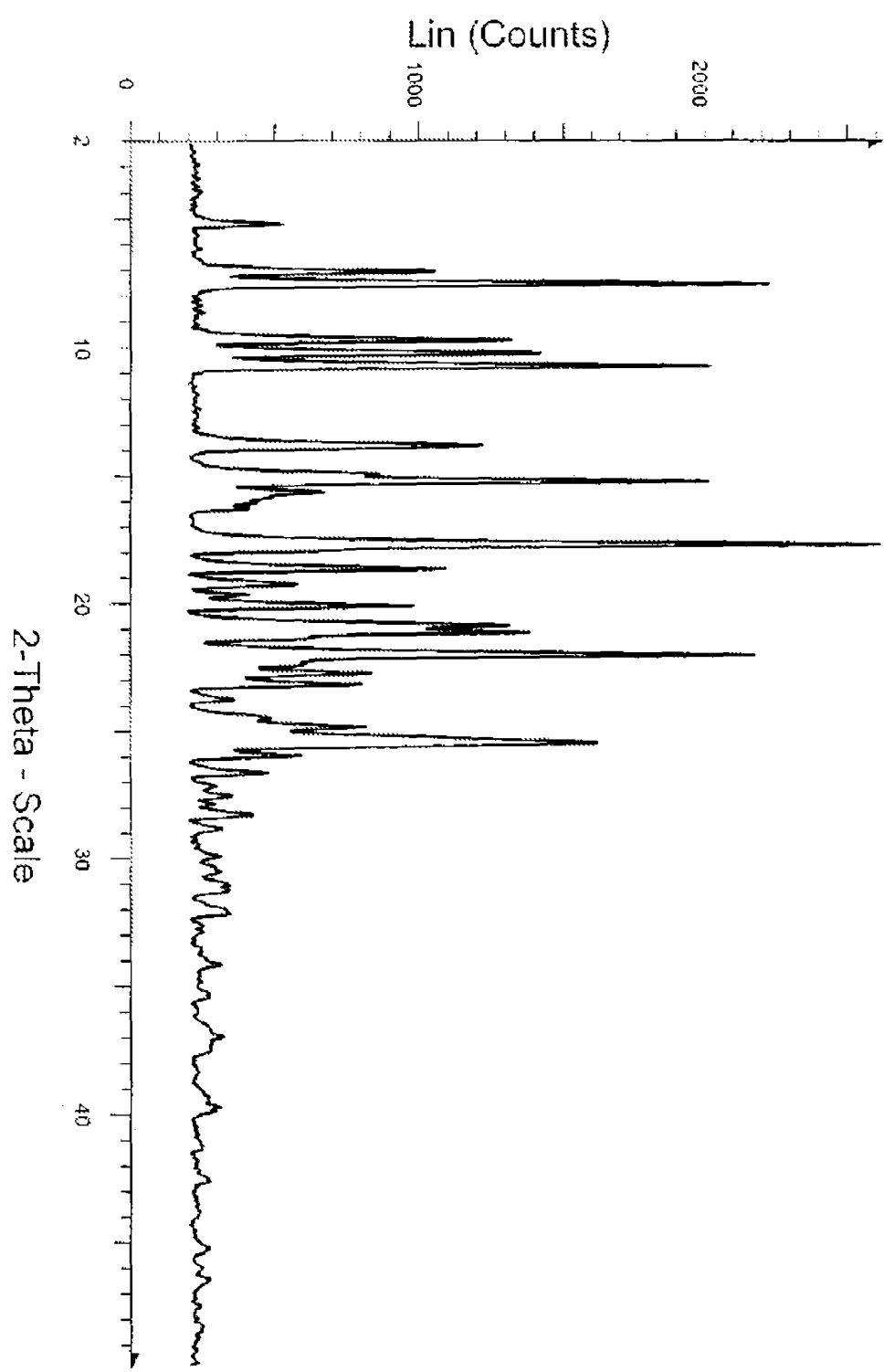
FIG. 2 shows powder X-ray diffractogram pattern of Selexipag isopropylamine crystalline salt.
Figure 3:
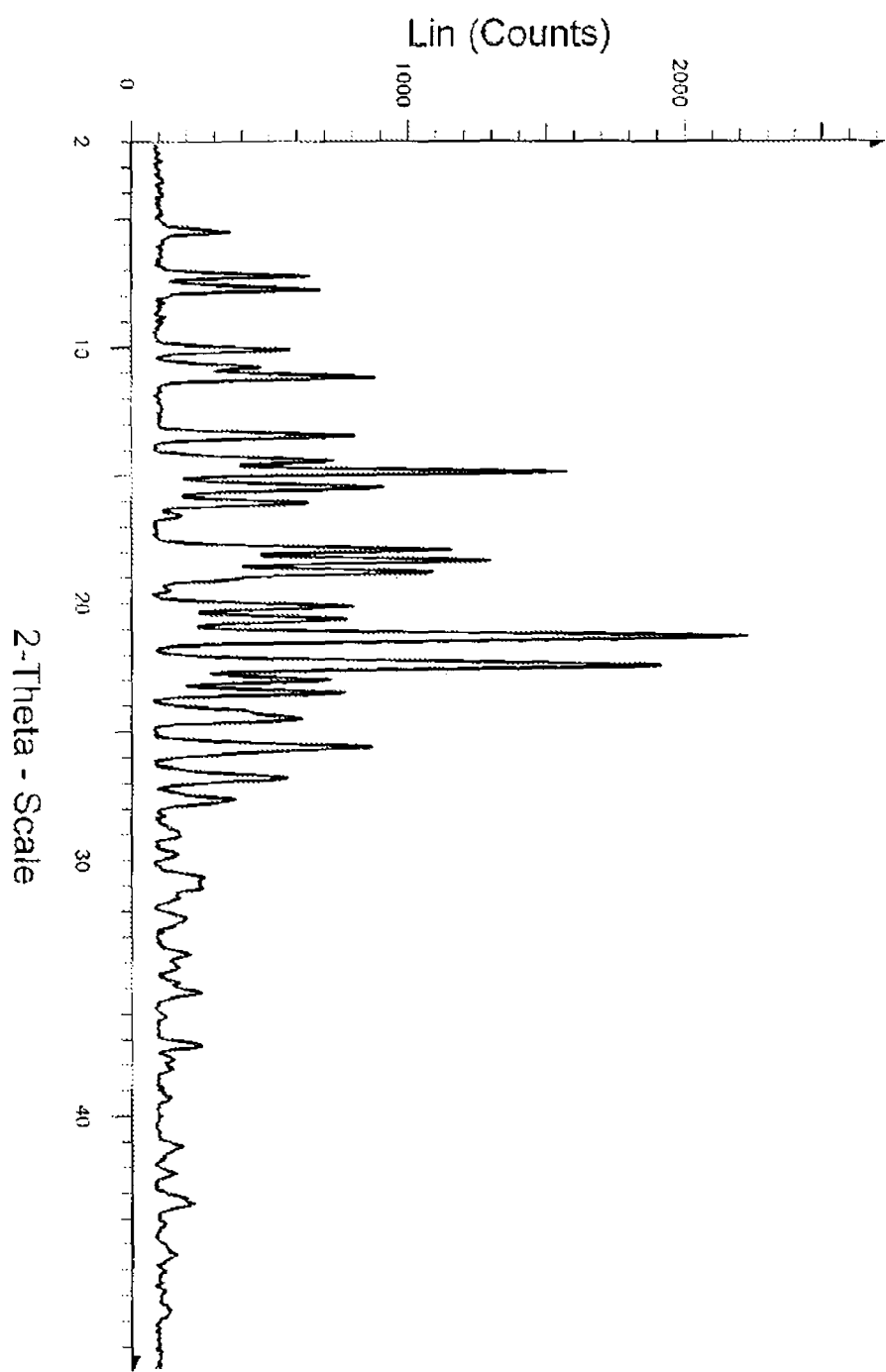
FIG. 3 shows powder X-ray diffractogram pattern of Selexipag N-methylmorpholine crystalline salt.
Figure 4:
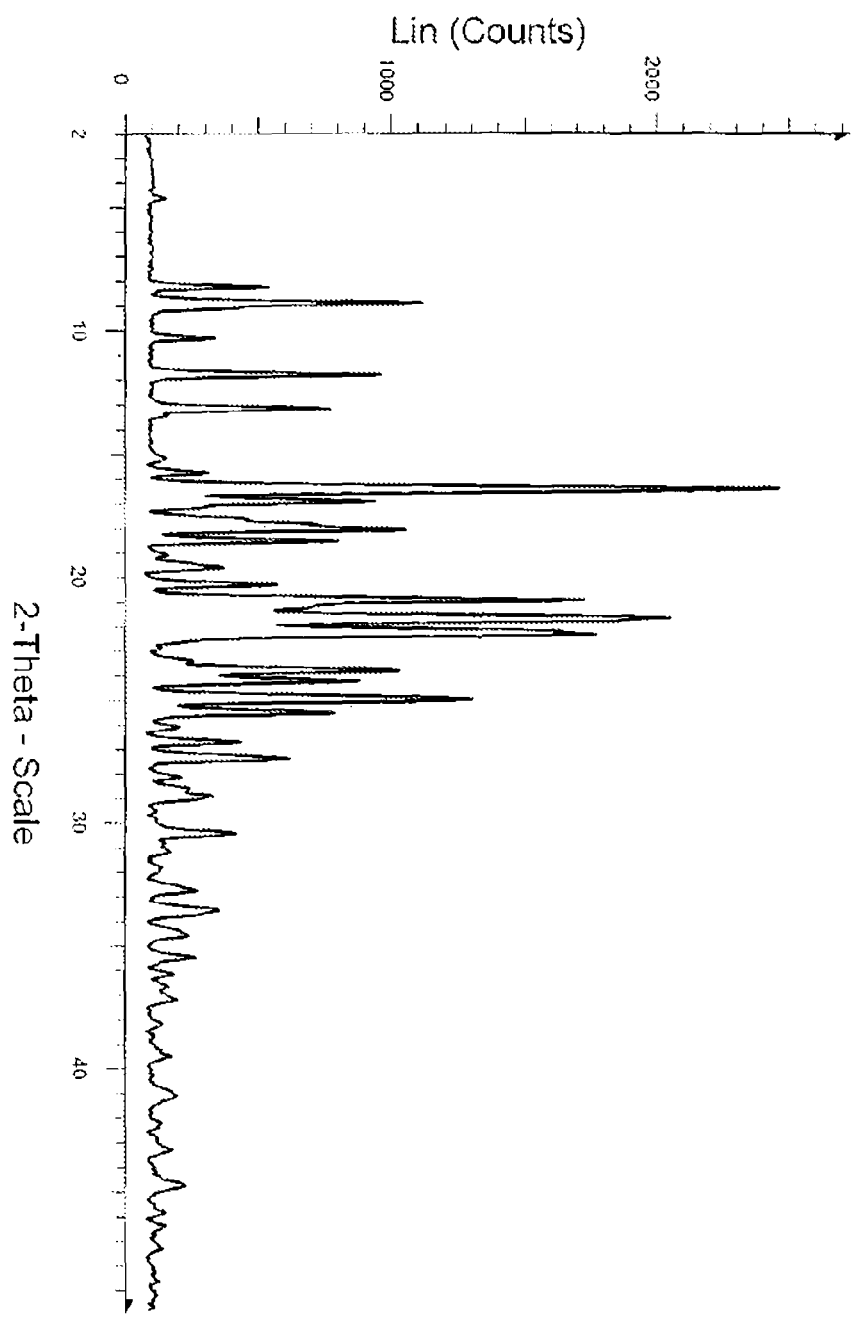
FIG. 4 shows powder X-ray diffractogram pattern of Selexipag diisopropylethylamine crystalline salt.
Figure 5:
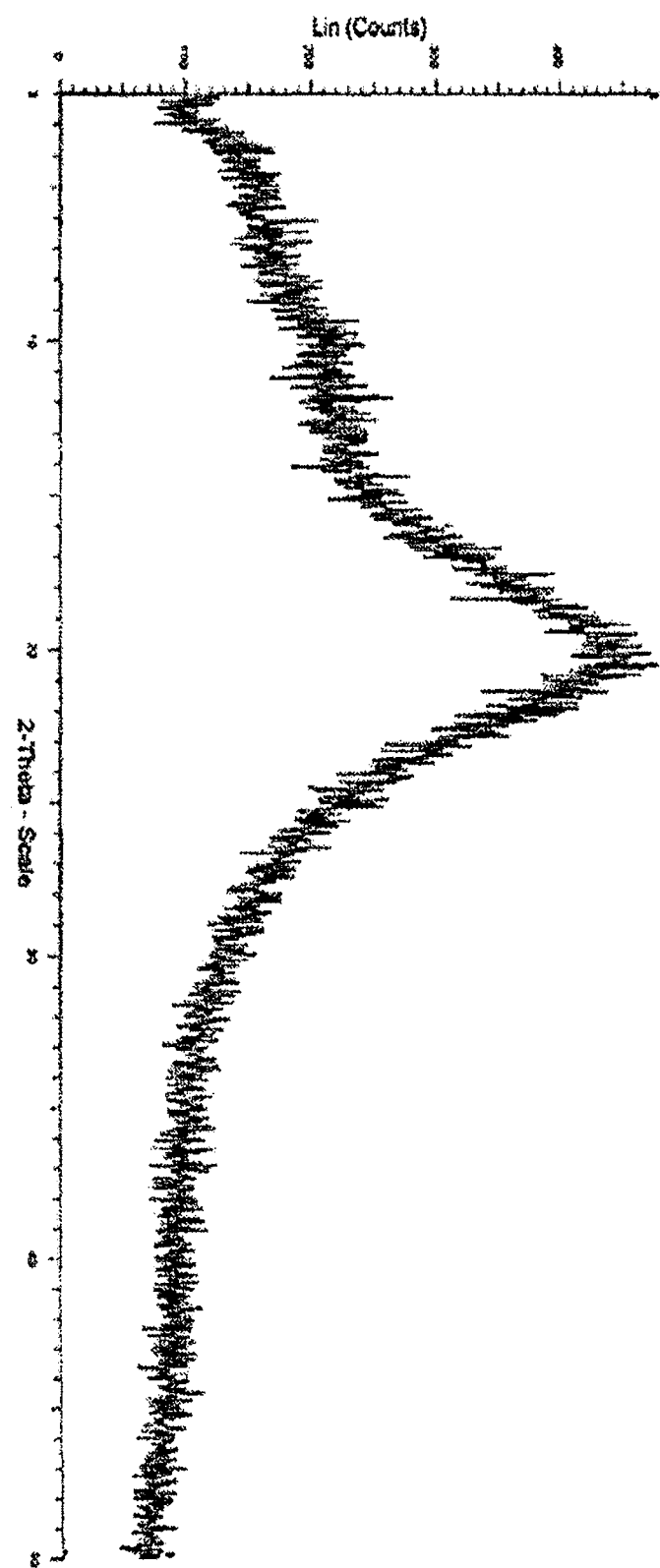
FIG. 5 shows powder X-ray diffractogram pattern of Selexipag amorphous form.

X-ray powder diffraction spectrum was measured on a bruker axs D8 advance X-ray powder diffractometer having a copper-a radiation. Adequate sample was gently flattered on a sample holder and scanned from 2 to 50 degrees two-theta, at 0.02 increment and scan speed of 0.2 Sec/Step. The sample was simply placed on the sample holder. The sample was rotated at 30 rpm at a voltage 40 KV and current 35 mA.

DETAILED DESCRIPTION OF THE INVENTION

The present invention relates to a process for the preparation of Selexipag which comprises: reacting the compound of formula II with a compound of formula III in the presence of condensing agent, wherein condensing agent is selected from the group comprising of 1-ethyl-3-(3-dimethylaminopropyl)carbodiimide, dicyclohexyl carbodiimide, diethyl cyanophosphonate, 1,1'-carbonyldiimidazole, diphenylphosphoryl azide and a solvent, wherein the solvent is an ester solvent, thereafter adjusting the pH of the reaction mass to 5.0-6.0 using a buffer, acetic acid; optionally the layers were separated and the organic solvent is removed to obtain Selexipag of Formula I.

In another aspect of the present invention, the pH of the reaction mass is adjusted to 5.0-6.0 with buffer, wherein buffer is selected from the group comprising of sodium dihydrogen phosphate, mono potassium phosphate, citric acid, boric acid, diethyl barbituric acid.

According to one aspect of the present invention, Selexipag triethylamine crystalline salt, which is characterized by Powder X-Ray Diffraction, having the characteristic °2θ, peaks at about 9.8, 15.2, 15.4, 17.9 and 21.5, ±0.2 degrees.

In another aspect the present invention provides a process for the preparation Selexipag triethylamine crystalline salt, which comprises:
a. treating Selexipag with triethylamine in a solvent; and
b. isolating the Selexipag triethylamine crystalline salt having the characteristic °2θ, peaks at about 9.8, 15.2, 15.4, 17.9 and 21.5, ±0.2 degrees.

According to one aspect of the present invention Selexipag isopropylamine crystalline salt, which is characterized by Powder X-Ray Diffraction, having the characteristic °2θ, peaks at about 7.4, 10.6, 15.1, 17.6, 21.9, ±0.2 degrees.

In another aspect the present invention provides a process for the preparation Selexipag isopropylamine crystalline salt, which comprises:
a. treating Selexipag with isopropylamine in a solvent; and
b. isolating the Selexipag isopropylamine crystalline salt having the characteristic °2θ, peaks at about 7.4, 10.6, 15.1, 17.6, 21.9, ±0.2 degrees.

According to one aspect of the present invention Selexipag tri n-butylamine crystalline salt, which is characterized by Powder X-Ray Diffraction, having the characteristic °2θ, peaks at about 9.4, 9.7, 16.9, 17.2, 20.2, 21.5, ±0.2 degrees.

In another aspect the present invention provides a process for the preparation Selexipag tri n-butylamine crystalline salt, which comprises:
a. treating Selexipag with tri n-butylamine in a solvent; and
b. isolating the Selexipag tri n-butylamine crystalline salt having the characteristic °2θ, peaks at about 9.4, 9.7, 16.9, 17.2, 20.2, 21.5, ±0.2 degrees.

According to one aspect of the present invention Selexipag N-methylmorpholine crystalline salt, which is characterized by Powder X-Ray Diffraction, having the characteristic °2θ, peaks at about 14.8, 21.2, 22.4, ±0.2 degrees.

In another aspect the present invention provides a process for the preparation Selexipag N-methylmorpholine crystalline salt, which comprises:
a. treating Selexipag with N-methylmorpholine in a solvent; and
b. isolating the Selexipag N-methylmorpholine crystalline salt having the characteristic °2θ, peaks at about 14.8, 21.2, 22.4, ±0.2 degrees.

According to one aspect of the present invention Selexipag diisopropylethylamine crystalline salt which is characterized by Powder X-Ray Diffraction, having the characteristic °2θ, peaks at about 16.3, 16.4, 21.6, 21.7, 22.2 ±0.2 degrees.

In another aspect the present invention provides a process for the preparation Selexipag diisopropylethylamine crystalline salt, which comprises:
a. treating Selexipag with diisopropylethylamine in a solvent; and
b. isolating the Selexipag diisopropylethylamine crystalline salt having the characteristic °2θ, peaks at about 16.3, 16.4, 21.6, 21.7, 22.2, ±0.2 degrees.

In another aspect of the present invention Selexipag is treated with a base at a temperature in in the range from 20° C. to 80° C.

In another aspect the present invention relates to a process for the preparation of Selexipag in amorphous form, which comprises: dissolving Selexipag crystalline salt in a low boiling solvent wherein the solvent is selected from the group comprising of methylenedichloride, diethylether, pentane, acetone, chloroform, hexane, methanol, tetrahydrofuran, optionally treating with a buffer, wherein buffer is selected from the group comprising of sodium dihydrogen phosphate, mono potassium phosphate, citric acid, boric acid, diethyl barbituric acid; acetic acid and removing the solvent to obtain Selexipag in amorphous form.

In another aspect of the present invention, the Selexipag is prepared by the condensation of compound of Formula II and III using a single solvent system.

In another aspect of the present invention, Selexipag is isolated as residue or solid as a crystalline or amorphous form.

In another aspect of the present invention, Selexipag amorphous form is stable at 5±3° C. and 25±2° C./RH (Relative humidity) 60±5%, 40±2° C./RH (Relative humidity) 75±5% and has the following stability data:

|  | PXRD | | | Chromatographic Purity (by HPLC) | | |
| --- | --- | --- | --- | --- | --- | --- |
|  | 5 ± 3° C. | 25 ± 2° C./ RH 60 ± 5% | 40 ± 2° C./ RH 75 ± 5% | 5 ± 3° C. | 25 ± 2° C./ RH 60 ± 5% | 40 ± 2° C./ RH 75 ± 5% |
| Initial | Amorphous | Amorphous | Amorphous | 99.63 | 99.63 | 99.63 |
| 1$^{st}$ month | Amorphous | Amorphous | Amorphous | 99.63 | 99.63 | 99.62 |
| 2$^{nd}$ Month | Amorphous | Amorphous | Amorphous | 99.66 | 99.59 | 99.58 |
| 3$^{rd}$ Month | Amorphous | Amorphous | Amorphous | 99.76 | 99.72 | 99.66 |
| 4$^{th}$ Month | Amorphous | Amorphous | — | 99.76 | 99.78 | 99.69 |
| 5$^{th}$ Month | Amorphous | Amorphous | — | 99.70 | 99.69 | 99.66 |
| 6$^{th}$ Month | Amorphous | — | — | 99.76 | 99.68 | 99.65 |

In another aspect of the present invention, desaltification of Selexipag crystalline salt is carried out at a temperature in the range from 20-30° C.

In another aspect of the present invention Selexipag crystalline salt contains 7-13% of salt content.

In another aspect of the present invention the solvent used in selexipag crystalline salt formation is ester solvent, wherein selected from the group comprising of ethyl acetate, methyl acetate, isopropyl acetate, tert-butyl methyl acetate, ethyl formate or mixtures thereof.

In another aspect of the present invention, the amorphous Selexipag obtained by removing the solvent by using suitable techniques which may be used for the removal of the solvent include evaporation techniques such as a Büchi® Rotavapor®, spray drying, agitated thin film drying, freeze drying (lyophilization) and the like or any other suitable technique of downward atmospheric distillation, the solvent may be removed, optionally under reduced pressures, at temperatures more than about 180° C., more than about 170° C., more than about 160° C., more than about 150° C., more than about 140° C., or any other suitable temperatures. The solvent may be removed optionally adjusting/the optimizing atmospheric pressure as well as temperatures.

Freeze drying (lyophilization) may be carried out by freezing a solution of Selexipag at low temperatures and reducing the pressure required to remove the solvent from the frozen solution of Selexipag. Temperatures that may be required to freeze the solution, depending on the solvent chosen to make the solution of Selexipag, may range from about −80° C. to about 0° C., or up to about 20° C. Temperatures that may be required to remove the solvent from the frozen solution may be less than about 20° C., less than about 0° C., less than about −20° C., less than about −40"C., less than about −60° C., less than about −80° C., or any other suitable temperatures.

In another aspect of the present invention, after removing the solvent, the obtained compound (which may be in the form of liquid, solid, semi-solid, gel) is subjected to melting, thereafter cooling to isolate the stable amorphous form of Selexipag.

In another aspect of the present invention, the reaction of Formula II with Formula III is carried out at a temperature in the range from 20° C. to 100° C.

In another aspect the present invention is advantageous over prior art as follows:
By using buffer, diimidazole related impurity washed out in water so there is no need of using column purification.
Single solvent (Isopropylacetate) is used during the condensation of Formula II and Formula III as well as for extraction and isolation. whereas by using multiple solvents for condensation and work-up 32 hours required
Time required is only 3-4 hours for the condensation of Formula II and Formula III.
1,8-Diazabicyclo[5.4.0.]-7-undecene was eliminated during condensation of Formula II and Formula III.
By using buffer for pH adjustment, there is no conversion of Selexipag to 2-(4-((5,6-diphenylpyrazin-2-yl)(isopropyl)amino)butoxy)acetic acid, whereas using HCl, the formation of 2-(4((5,6-diphenylpyrazin-2-yl)(isopropyl)amino)butoxy)acetic acid is up to 16-20%.

In the following section embodiments are described by way of examples to illustrate the process of invention. However, these do not limit the scope of the present invention. Variants of these examples would be evident to persons ordinarily skilled in the art.

EXAMPLES

Reference Example

Preparation of 2-{4-[N-(5,6-diphenylpyrazin-2-yl)-N-isopropylamino]butyloxy}-N-(methylsulfonyl) acetamide 21.07 g of 2-{4-[N-(5,6-diphenylpyrazin-2-yl)-N-isopropylamino]butyloxy}acetic acid tert-butyl ester was dissolved in 200 ml of methanol and 60 ml of 1N sodium hydroxide solution was added. After the mixture was heated at reflux for 2 hours, the solvent was evaporated under reduced pressure and the residue was dissolved in water. After washing with diethyl ether, the aqueous layer was neutralized with 60 ml of 1N hydrochloric acid and then extracted with ethyl acetate. The extract was dried over anhydrous magnesium sulfate and the solvent was evaporated under reduced pressure, and then the residue was washed with diisopropyl ether to obtain 15.82 g of the desired compound.

Under an argon atmosphere, to a solution of 300 mg of 2-{4-[N-(5,6-diphenylpyrazin-2-yl)-N-isopropylamino]butyloxy}acetic acid in 5 ml of anhydrous tetrahydrofuran, 128 mg of 1,1'-carbonyl diimidazole was added and, after stirring at room temperature for 30 minutes, the mixture was heated at reflux for 30 minutes. After air-cooling to room temperature, 69 mg of methanesulfonamide was added. After stirring for 10 minutes, 0.11 ml of 1,8-diazabicyclo[5.4.0.]-7-undecene was added dropwise. After stirring at room temperature overnight, the reaction solution was diluted with water and then extracted with diethyl ether. The extract was dried over anhydrous magnesium sulfate and the solvent was evaporated under reduced pressure, and then the residue was purified by silica gel column chromatography to obtain 272 mg of the desired compound.

Example 1

Preparation of 2-{4-[N-(5,6-diphenylpyrazin-2-yl)-N-isopropylamino]butyloxy}-N-(methylsulfonyl)acetamide (Selexipag)

Preparation of 5,6-diphenylpyrazin-2(1H)-one

To Glycinamde hydrochloride (263 gm) in methanol added sodium hydroxide solution at 10-15° C. Added dibenzil (500 gm) lot wise and stirred for 3 hours to 3 hours 30 minutes and adjusted the pH of the reaction mass with dilute HCl. Filtered the solid thus separated, washed with methanol and dried to yield 5,6-diphenylpyrazin-2(1H)-one (520 gm) (Purity by HPLC: 99.31%).

Preparation of 5-Chloro-2,3-diphenylpyrazine

To 5,6-diphenylpyrazin-2(1H)-one (500 gm), added POCl₃ (2500 ml) at 20-25 deg C. and stirred for 10 hours to 12 hours at reflux. Cooled and then the pH was adjusted to neutral. Filtered the solid thus separated, washed with methanol and dried to yield 5-Chloro-2,3-diphenylpyrazine.
Yield: 520 gm
Chromatographic Purity (by HPLC): 99.43%

Preparation of 4-(5,6-diphenylpyrazin-2-yl)isopropyl)(amino)butan-1-ol

5-Chloro-2,3-diphenylpyrazine (300 gm), 4-isopropylaminobutanol (443 gm) were taken and then heated to 170-195° C., stirred for 10 hours to 12 hours and further cooled to 25-30° C. Then added water, extracted with methyl tert-butyl ether, dried the organic layer and concentrated to obtain the desired compound.
Yield: 252 gm
Chromatographic Purity (by HPLC): 99.01%

Preparation of tert-butyl 2-(4-(5,6-diphenylpyrazin-2-yl)isopropyl)(amino)butoxy) acetate To 4-(5,6-diphenylpyrazin-2-yl)isopropyl)(amino)butan-1-ol (75 gm) in toluene added tetrabutyl ammonium hydrogen sulfate (35.2 gm) at 20-25° C. Further added 40% potassium hydroxide (560 ml) solution dropwise and tert-butyl bromoacetate (121.4 gm) dropwise at 0-5° C., stirred for 1 hour to 1 hour 30 minutes and diluted with water, extracted with methyl tert-butyl ether. The organic layer was dried and distilled off to yield tert-butyl 2-(4-(5,6-diphenylpyrazin-2-yl) isopropyl)(amino)butoxy)acetate
Yield: 91 gm
Chromatographic Purity (by HPLC): 98.35%

Preparation of 2-{4-[N-(5,6-diphenylpyrazin-2-yl)-N-isopropylamino]butyloxy}acetic Acid To tert-butyl 2-(4-(5,6-diphenylpyrazin-2-yl) isopropyl) (amino)butoxy)acetate (100 gm) in methanol added 1N sodium hydroxide (320 ml) solution and stirred for 1 hour to 2 hours at 80-85° C. Cooled to 30° C. and diluted with water. The pH of the reaction mass was adjusted with dilute HCl, filtered the solid thus separated, washed with water and dried to yield of desired compound.
Yield: 75 gm
Chromatographic Purity (by HPLC): 98.74%

Preparation of 2-{4-[N-(5,6-diphenylpyrazin-2-yl)-N-isopropylamino]butyloxy}-N-(methylsulfonyl)acetamide (Selexipag)

To a solution of 2-{4-[N-(5,6-diphenylpyrazin-2-yl)-N-isopropylamino]butyloxy}acetic acid (100 gm) in isopropylacetate (1600 ml) added 1,1'-Carbonyldiimidazole (58 gm) at 20-25° C. and stirred for 30 minutes under nitrogen atmosphere. Added methanesulfonamide (34 gm) at 20-25° C. and stirred for 3 hours to 4 hours at 90-95° C. Cooled to 10-15° C. and the pH of the reaction mass was adjusted to 5.0-6.0 with sodium dihydrogen phosphate. The layers were separated, dried the organic layer and distilled off the solvent to obtain 120 gm of residue.

Preparation of Selexipag triethylamine salt

The residue obtained was dissolved in isopropyl acetate (500 ml) and triethylamine (33.7 gm) was added, heated to 90-95° C. for 1 hour and then allowed to 25-30 deg C. and stirred for 1-2 hours. Thereafter the crystals were collected by filtration and dried to obtain Selexipag triethylamine salt.
Yield: 108 gm
Chromatographic Purity (by HPLC): 99.05%

Preparation of Selexipag

Selexipag triethylamine salt was dissolved in dichloromethane (1000 ml) and washed with sodium dihydrogen phosphate at 25-30° C. The layers were separated, dried the organic layer and distilled off the solvent to obtain amorphous Selexipag.
Yield: 90 gm
Chromatographic Purity (by HPLC): 99.61%

Example 2

Preparation of Selexipag Isopropylamine Salt

Selexipag (5.0 gm; 1.0 eq) was dissolved in isopropyl acetate (25 ml) and Isopropylamine (1.4 eq) was added, heated to 90-95° C. for 1 hour and further allowed to 25-30 deg C. and stirred for 1-2 hours. Thereafter the crystals were collected by filtration and dried to obtain Selexipag Isopropylamine salt.

Yield: 4.5 gm
Chromatographic Purity (by HPLC): 98.89%

Example 3

Preparation of Selexipag N-Methylmorpholine Salt

Selexipag (5.0 gm; 1.0 eq) was dissolved in isopropyl acetate (25 ml) and N-Methylmorpholine (1.4 eq) was added, heated to 90-95° C. for 1 hour and further allowed to 25-30 deg C. and stirred for 1-2 hours. Thereafter the crystals were collected by filtration and dried to obtain Selexipag N-Methylmorpholine salt.

Yield: 4.5 gm
Chromatographic Purity (by HPLC): 99.19%

Example 4

Preparation of Selexipag Diisopropylethylamine Salt

Selexipag (5.0 gm; 1.0 eq) was dissolved in isopropyl acetate (25 ml) and diisopropylethylamine (1.4 eq) was added, heated to 90-95° C. for 1 hour and further allowed to 25-30 deg C. and stirred for 1-2 hours. Thereafter the crystals were collected by filtration and dried to obtain Selexipag diisopropylethylamine salt.

Yield: 4.5 gm
Chromatographic Purity (by HPLC): 99.44%

Example 5

Preparation of Selexipag Tri n-Butylamine Salt

Selexipag (5.0 gm; 1.0 eq) was dissolved in isopropyl acetate (25 ml) and tri n-butylamine (1.4 eq) was added, heated to 90-95° C. for 1 hour and further allowed to 25-30 deg C. and stirred for 1-2 hours. Thereafter the crystals were collected by filtration and dried to obtain Selexipag tri n-butylamine salt Yield: 4.5 gm
Chromatographic Purity (by HPLC): 99.54%

Example 6

Preparation of Selexipag

Selexipag triethylamine salt (100 gm) was dissolved in dichloromethane (1000 ml), stirred for 10 minutes at 25-30° C. and passed through hyflo bed. Further added acetic acid solution and stirred. The layers were separated and the organic layer was passed through 0.5 µm filter. Distilled off the solvent under vacuum and dried for 3 hours to 4 hours under vacuum. Slowly raised the temperature to 145-150° C. and allowed to room temperature under vacuum. Further cooled to below 0° C. to obtain amorphous selexipag.

Yield: 70 gm
Chromatographic Purity (by HPLC): 99.76%

We claim:

1. A process for the preparation of Selexipag compound of formula I, which comprises:

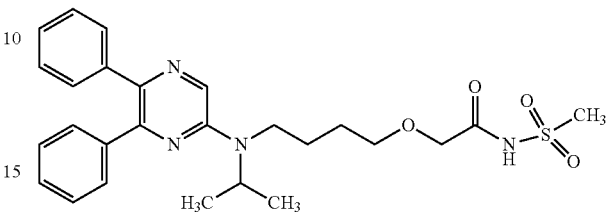

Formula I a. reacting the compound of formula II,

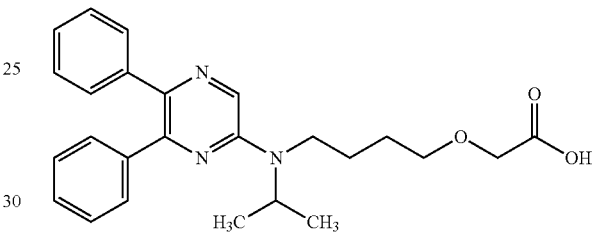

Formula II with a compound of formula III,

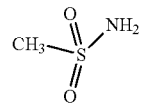

Formula III in the presence of a condensing agent and a solvent;
b. adjusting the pH of the reaction mass using a buffer;
c. separating the layers obtained from step b and removing the solvent; and
d. isolating the Selexipag of Formula I.

2. The process according to claim 1, wherein the solvent used is an ester selected from the group consisting of ethyl acetate, methyl acetate, isopropyl acetate, tert-butyl methyl acetate, ethyl formate, and mixtures thereof.

3. The process according to claim 1, wherein the condensing agent is selected from the group consisting of 1-ethyl-3-(3-dimethylaminopropyl)carbodiimide, dicyclohexyl carbodiimide, diethyl cyanophosphonate, 1,1'-carbonyldiimidazole, and diphenylphosphoryl azide.

4. The process according to any one of claim 1, 2, or 3, wherein the buffer is selected from the group consisting of sodium dihydrogen phosphate, mono potassium phosphate, citric acid, boric acid, acetic acid, and diethyl barbituric acid.

* * * * *